United States Patent [19]

Patterson

[11] 4,283,143

[45] Aug. 11, 1981

[54] OPTICAL CHARACTERIZATION OF A SUSPENSION

[75] Inventor: James A. Patterson, Los Altos, Calif.

[73] Assignee: Amco Standards International, Mountain View, Calif.

[21] Appl. No.: 95,578

[22] Filed: Nov. 19, 1979

[51] Int. Cl.³ .......................................... G01M 15/02
[52] U.S. Cl. .................................. 356/336; 356/339
[58] Field of Search ............................... 356/336, 339

[56] References Cited

PUBLICATIONS

Gledhill, "Particle-Size Distribution Determination by Turbidimetry", *Journal of Physical Chemistry*, v. 66, pp. 458–463, Mar. 1962.

*Primary Examiner*—John K. Corbin
*Assistant Examiner*—Matthew W. Koren
*Attorney, Agent, or Firm*—Limbach, Limbach & Sutton

[57] ABSTRACT

A method of determining the percent solids and particle size distribution of a liquid suspension is taught. A purely optical method of making these determinations is disclosed which is independent of the physical nature of the particles in suspension.

2 Claims, 4 Drawing Figures

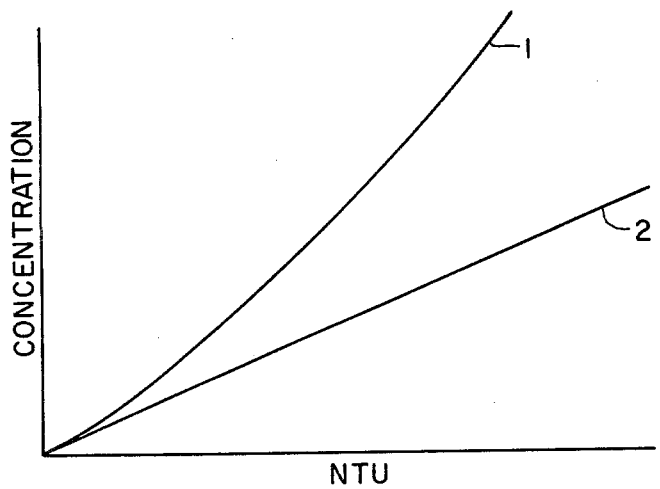
FIG._1.
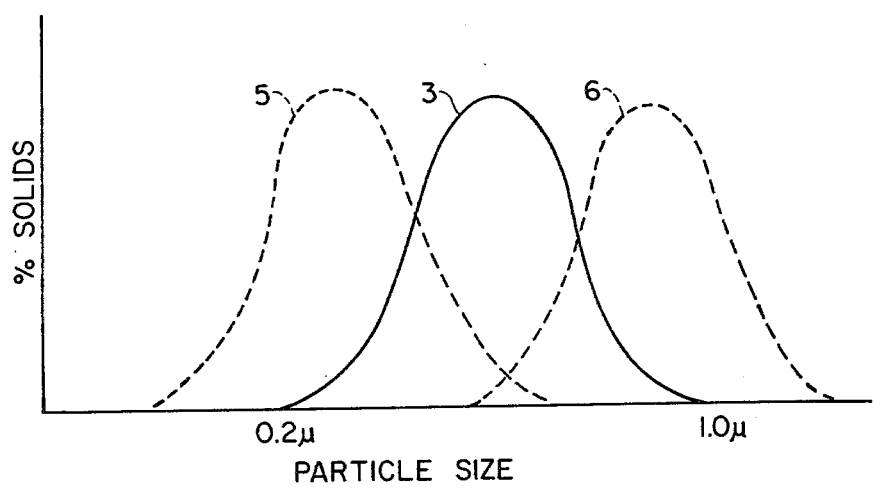
FIG._2.

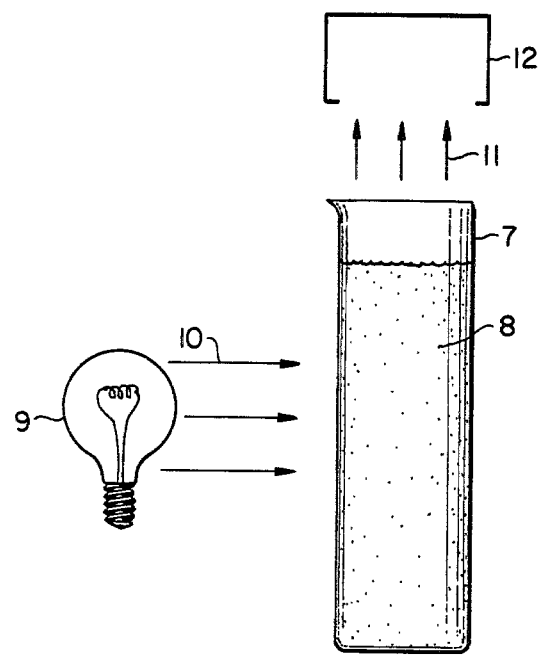
FIG._3.
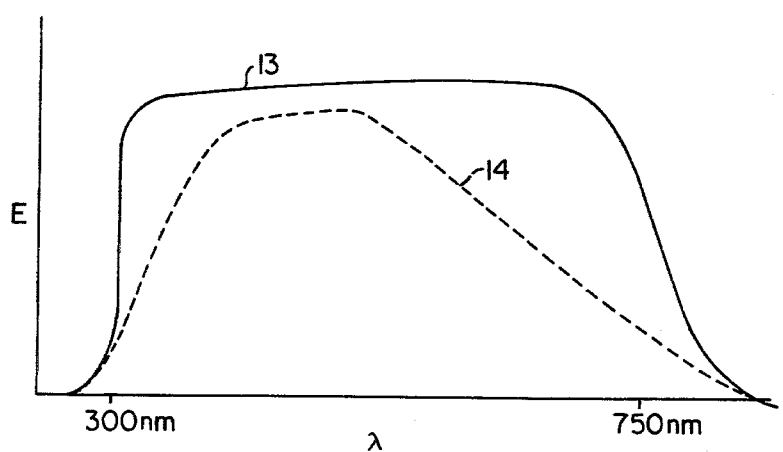
FIG._4.

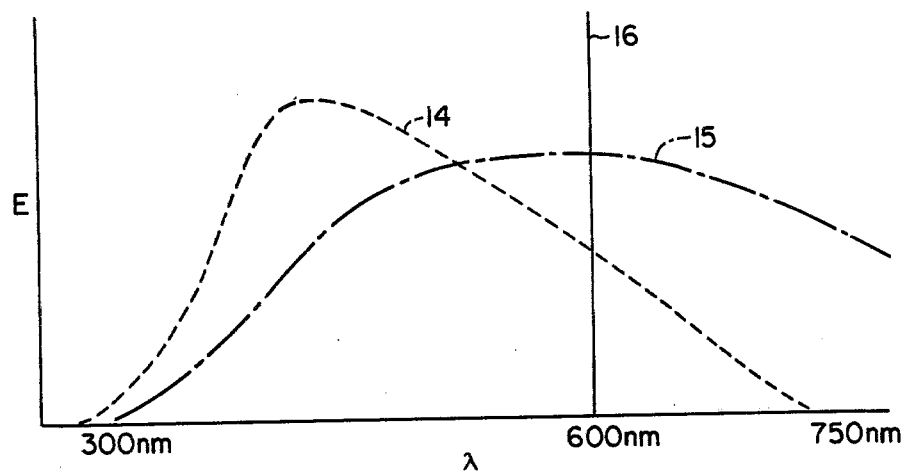
FIG._5.

OPTICAL CHARACTERIZATION OF A SUSPENSION

BACKGROUND OF THE INVENTION

In co-pending Application Ser. No. 933,140 filed on Aug. 14, 1978 entitled STYRENE-DIVINYLBENZENE COPOLYMER AND METHOD OF MANUFACTURE, a means of accurately determining the turbidity of a liquid media, such as water, was taught. In testing and treating water for drinking purposes, it is necessary to test the water's turbidity. Turbidity has a marked effect on the bacteriological quality of water, whether or not disinfection is practiced. This is so because turbidity interferes with the ability to disinfect water.

In addition to the determination of turbidity, it was found to also be advantageous to determine the particle size distribution of suspended particles in the liquid media and the concentration of said suspended particles. Prior to this invention, one responsible for the treatment of drinking water with, for example, chlorine, would add a specific amount of chlorination depending upon the turbidity values encountered. However, applicant has discovered that as the particle size distribution increases, less chlorination is needed for a specific turbidity reading. Thus, a measurement of not only the turbidity but also the particle size distribution of suspended solids in drinking water would result in minimizing the amount of chlorine necessary to yield safe drinking water which would in turn allow filters to last longer, minimize the need for polyelectrolyte flocking agents and would minimize the time needed to retain the drinking water in classifiers. Furthermore, as an excess of chlorine is added to water, the colloidal particles become overloaded with chlorine which in turn become a polutant.

Attempts to directly relate the turbidity of a known standard with that of an unknown in order to determine concentration or particle size distribution have previously proved unsuccessful. This is because the degree of light scatter of a liquid suspension depends not only upon the concentration of the suspended solids, but also the size and distribution of suspended solids, the existence of dissolved materials (salts and non-ionics), the geometry of suspended solids, the color of the liquid media and suspended solids and the index of refraction of the media and suspended solids. Thus, it has been virtually impossible to optically determine the concentration or particle size distribution of a liquid suspension optically.

SUMMARY OF THE INVENTION

It is thus an object of the present invention to determine the concentration and particle size distribution of suspended solid particles in a liquid media optically.

It is yet another object of the present invention to determine the particle size distribution and concentration of solid particles in a liquid media without knowing the physical characteristics of the suspended solids or liquid media.

This and other objects will be further appreciated when considering the following specification and drawings wherein FIG. 1 is a graph showing the relationship between concentration and NTU for an unknown liquid suspension;

FIG. 2 is a graph of the particle size distribution of standard styrene-divinyl benzene copolymers;

FIG. 3 shows practicing the method of the present invention through the measure of light scatter;

FIG. 4 is a graph of the energy output of a light source as a function of wavelength; and FIG. 5 is a graph of the energy received by a photomultiplier as a function of wavelength.

In co-pending Application Ser. No. 933,140, the disclosure of which is incorporated herein by reference, a definitive standard for use in the measurement of turbidity of a liquid such as water was presented which comprises the use of a unique styrene-divinylbenzene copolymer suspended in a substantially pure aqueous media. The Environmental Protection Agency adopted the invention disclosed in U.S. Application Ser. No. 933,140 as the definitive means of testing the turbidity of water. The use of that invention has been coined the Nephelometric Method and measurements made using it are reported in Nephelometric Turbidity Units (NTU). The standard proved to be so reproducable that one can relate NTU with concentration of the styrene-divinylbenzene copolymers as follows:

| 90° Light Scatter vs Concentration | |
|---|---|
| NTU | p/ml (particles/milliliter) |
| 0.95 | $1.42 \times 10^8$ |
| 1.9 | $2.85 \times 10^8$ |
| 3.8 | $5.70 \times 10^8$ |
| 7.8 | $1.14 \times 10^9$ |
| 15.0 | $2.25 \times 10^9$ |
| 29.0 | $4.38 \times 10^9$ |
| 57.3 | $8.60 \times 10^9$ |
| 103.7 | $1.56 \times 10^{10}$ |
| 170.0 | $2.55 \times 10^{10}$ |
| 224.0 | $3.38 \times 10^{10}$ |

One would logically assume that a comparison of the NTU value of a specific liquid suspension with the standard recited above would yield the solid particle concentration. However, as stated previously, a direct optical comparison is difficult due to the physical characteristics of the suspended solids and liquid media. Applicants have developed a method, however, for accounting for these physical characteristics as follows.

CONCENTRATION OF SUSPENDED PARTICLES

A specific quantity of a known concentration of a standard is placed within an indexed cuvette and the NTU value read therefrom according to the disclosure of co-pending Application Ser. No. 933,140. In this illustration, 1.0 ml of 100.0 NTU of the standard is placed in 100.0 ml of pure water. Theoretically, the value of 1.0 NTU should be achieved, however, a true reading of 1.05 NTU is read because the total volume in the cuvette is 101.0 ml, not 100.0 ml. A specific quantity of the unknown liquid suspension is added to a clean cuvette and the NTU reading is taken. In this illustration, the unknown sample was selected to have a volume of 100.0 ml. After the NTU reading was taken, exactly 1.00 ml of 100.0 NTU was added and a second reading was taken. For additional accuracy, one could use several samples of the unknown in different cuvettes and the NTU readings then averaged. Theoretically, the unknown liquid suspension should have exhibited the same increase in NTU value as was displayed by adding the equivalent amount of standard to the reference of substantially pure water, i.e., an increase of 1.05 NTU. However, the liquid suspension shows a different value which accounts for the physical characteristics of the suspended solids and aqueous media such as the size and distribution of suspended solids, dissolved materials, geometry of the suspended solids, color of the media and suspended solids and index of refraction of the media and suspended solids. In this example, an initial NTU of 5.35 was observed with an NTU, after the addition of 1.00 ml of 100.0 NTU standard of 5.75. The increase in NTU was 0.40 which is an attenuation of 0.65 NTU (1.05−0.40). The correction factor or turbidity nephelometric index is established at 0.40÷1.05=0.38. To thus correct the original nephelometric turbidity reading of the unknown suspension, one merely divides the NTU reading by the turbidity nephelometric index factor 5.35 NTU÷0.38=14.08 NTU.

Turning to FIG. 1 a graph is displayed which shows the relationship between concentration and NTU for an unknown liquid suspension. If one were to take NTU readings for various concentrations of the suspension, one would generate non-linear curve 1. The non-linearity of curve 1 is due to the fact that the physical characteristics of the media and suspended solids cause the NTU reading to change at different rates for a given change in concentration depending upon the size of the suspended particles. However, once the turbidity nephelometric index has been established so that one corrects the nephelometric turbidity readings, one would generate straight line 2. Therefore, if one were to practice the method outlined above, wherein the nephelometric turbidity was read for an unknown suspension at two different concentrations, one would generate line 2 and could then project a linear function to determine the concentration of any unknown liquid suspension at any specific nephelometric turbidity reading.

In summary of the above discussion, applicant has discovered a method of determining particle concentration of an unknown liquid suspension comprising the determination of the nephelometric turbidity reading for an unknown liquid suspension, correction of the nephelometric turbidity reading of the unknown liquid suspension to account for the physical characteristics of the suspended solids and liquid media, and the determination of the nephelometric turbidity reading for the unknown liquid suspension at a different concentration of suspended solids in liquid media to establish a linear relationship between the corrected nephelometric turbidity reading and concentration of the unknown liquid suspension.

PARTICLE SIZE DISTRIBUTION

In co-pending Application Ser. No. 933,140, it is taught that the particle size distribution of the standard styrene-divinylbenzene copolymer in a substantially pure aqueous carrier has an average diameter of between 0.2µ to 1.0µ. Plotted on a graph of percent solids versus particle size, the distribution takes the shape of bell curve 3 (FIG. 2). Of primary importance here is the corresponding particle size distribution of an unknown liquid suspension. The particle size distribution of the unknown could be greater or less than that of the standard and a representation of the particle size distribution of the unknown could therefore be represented by curves 6 or 5, respectively.

In beginning this method, indexed cuvettes are prepared to determine the NTU value for both the standard and the unknown suspensions as previously discussed. Referring to FIG. 3, cuvette 7 containing suspension 8 is illuminated by light source 9 as shown schematically by light beams 10. Scattered light eminating from the suspension shown schematically at 11 is picked up via photomultiplier 12.

Referring to FIG. 4, the output of a light source can be plotted in a graph of energy vs. wave length. Although any light source may be used, curve 13 depicts the typical energy output of a tungsten light source radiating at approximately 3,000° K. When the standard reference suspension of a styrene-divinylbenzene copolymer in a pure aqueous liquid is placed between the light source and photomultiplier, the energy spectrum read by the photomultiplier is shown by curve 14. The reason for the energy tail-off is because the suspended particles are more responsive to infrared radiation.

The same photomultiplier can be used to observe the light scattering of the unknown suspension. The readings of the photomultiplier, however, are not directly usable for the light scatter of the suspension will reflect the physical nature of the materials, and will be distorted by the geometry of the suspended solids, color of the media and the suspended solids and index of refraction of the media and suspended solids. These physical characteristics can be corrected as described previously in calculating a factor known as the turbidity nephelometric index. This factor can then be used to correct the photomultiplier output reading to allow direct comparison with the output of the standard suspension.

Turning to FIG. 5, on a single graph can be plotted line 14 representing the photomultiplier reading for the standard suspension and a corresponding reading 15 for the unknown suspension corrected by the turbidity nephelometric index. If a filter is placed between the photomultiplier and cuvette, one can directly compare the particle size distribution shown schematically at 16. In this particular example, at 600 nm, the unknown has a slightly larger particle size than the divinylbenzene-styrene copolymer of the standard suspension. Various filters of different wave length can be used to determine the particle size distribution of the unknown suspension over the entire spectrum.

The area embraced by curves 14 or 15 can be mathematically depicted as follows:

$$\int_{750}^{300} \frac{dI}{d\lambda} = \text{area under curve 15} =$$

NTU (Turbidity Nephelometric Units)

Thus, the integral of light intensity, dI at a specific wave length is equal to the corrected NTU value. Knowing this allows one to gain insight into the particle size of the suspended solids of the unknown versus that of the referenced suspension. For example, one could take the ratio of the NTU for the standard to NTU of the unknown and compare that to the corresponding ratio when a filter is used before the photomultiplier (see FIG. 5). If the ratio without the filter is greater than the ratio with the filter, it is known that the size distribution of suspended solids in the unknown suspension is larger than the standard.

The present invention is also adaptable for computer implementation wherein a large number of blocking filters of different frequency response could be used in a given system and the information then fed into a computer which would generate an exact particle size comparison at all frequencies.

Although the present invention was described in terms of the use of a tungsten light source and photomultiplier pickup, virtually any other equipment which would perform the same result can be used. Furthermore, the utility of the present invention was specifically described in terms of drinking water and the decision to add chlorine based upon the physical nature of the suspended particles. However, the present invention can also be used any time it is important to know the concentration or particle size distribution of a liquid suspension. For example, the present invention can be employed in wine making, in the testing of medical preparations, in grinding, cooking and lubricating oils and in jet fuels. In general, the present invention can be used in any environment wherein suspended particulate matter is required or is considered a pollutant.

What is claimed is:

1. A method of determining the particle size distribution of an unknown liquid suspension comprising:
   A. determining the nephelometric turbidity reading for a known standard liquid suspension;
   B. determining the nephelometric turbidity reading for an unknown liquid suspension;
   C. measuring the light scattering energy of the standard and unknown liquid suspensions;
   D. correcting the light scattering energy of the unknown liquid suspension for the physical characteristics of the suspended solids and liquid media; and
   E. comparing the corrected light scattering energy of the unknown liquid suspension with the light scattering energy of the standard suspension.

2. A method of determining particle concentration of an unknown liquid suspension comprising:
   A. determining the nephelometric turbidity reading for an unknown liquid suspension;
   B. correcting the nephelometric turbidity reading of the unknown liquid suspension for the physical characteristics of the suspended solids and liquid media;
   C. repeating step A for the unknown liquid suspension at a different concentration of suspended solids in liquid media to establish a linear relationship between the corrected nephelometric turbidity reading and concentration of the unknown liquid suspension.

* * * * *